(12) United States Patent
Franz

(10) Patent No.: US 7,376,217 B2
(45) Date of Patent: May 20, 2008

(54) OPERATING METHODS FOR A MEDICAL IMAGING SYSTEM AND FOR A COMPUTING DEVICE, AND DEVICES CORRESPONDING THERETO

(75) Inventor: Michael Franz, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 502 days.

(21) Appl. No.: 10/939,318

(22) Filed: Sep. 10, 2004

(65) Prior Publication Data

US 2005/0058243 A1 Mar. 17, 2005

(30) Foreign Application Priority Data

Sep. 11, 2003 (DE) .................. 103 42 245

(51) Int. Cl.
*G01N 23/04* (2006.01)
(52) U.S. Cl. ............................. 378/62; 378/901
(58) Field of Classification Search .............. 378/62, 378/51–63, 98, 98.2, 901
See application file for complete search history.

(56) References Cited

U.S. PATENT DOCUMENTS

| | | | |
|---|---|---|---|
| 6,363,134 B1 * | 3/2002 | Suzuki ................. | 378/15 |
| 6,816,564 B2 * | 11/2004 | Charles et al. ........... | 378/5 |
| 6,847,697 B2 * | 1/2005 | Kurahashi ............. | 378/62 |
| 6,907,099 B2 * | 6/2005 | Kling et al. ........... | 378/4 |
| 2002/0019751 A1 | 2/2002 | Rothschild et al. ........ | 705/3 |
| 2002/0029264 A1 * | 3/2002 | Ogino et al. ............ | 709/223 |
| 2003/0091157 A1 * | 5/2003 | Nakanishi et al. ......... | 378/205 |
| 2003/0194117 A1 * | 10/2003 | Okuzawa ............... | 382/128 |
| 2004/0022349 A1 * | 2/2004 | Hagiwara .............. | 378/4 |
| 2004/0120557 A1 * | 6/2004 | Sabol et al. ............ | 382/128 |

* cited by examiner

*Primary Examiner*—Edward J. Glick
*Assistant Examiner*—Alexander H Taningco

(57) ABSTRACT

A control device (4) for a medical imaging system drives a signal source (1) and a detector (2) so that the detector (2) registers raw data of an object (5). Said device accepts the registered raw data and conveys send data corresponding to said registered raw data via a computer-to-computer link (10) to a computing device (11) not assigned to the medical imaging system. Said device determines an end data record by means of the send data and conveys it to the control device (4) via the computer-to-computer link (10). At least one end image is defined by the end data record. The control device (4) feeds out the end image to a user (15) of the medical imaging system via a viewing device (16).

15 Claims, 6 Drawing Sheets

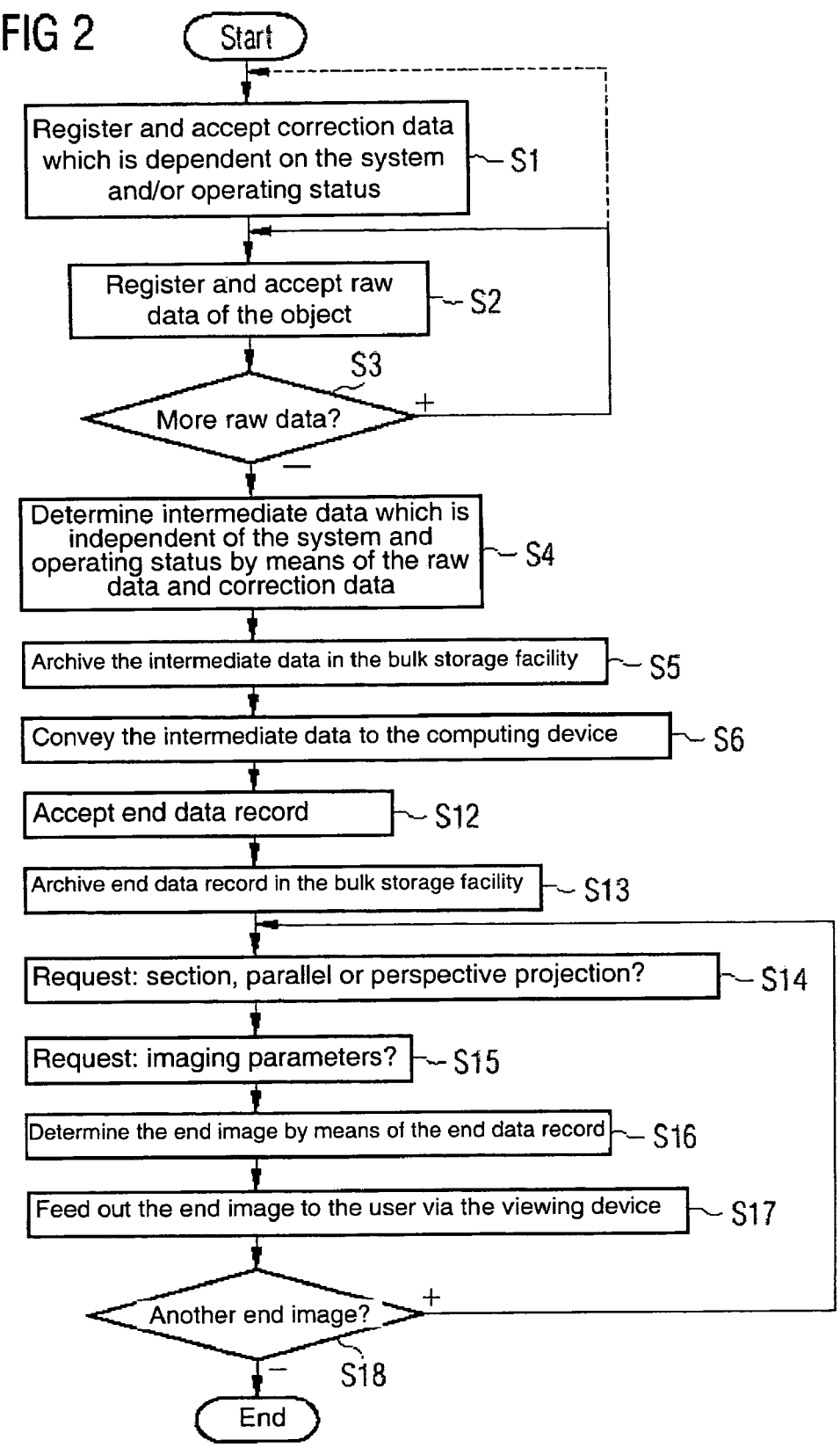

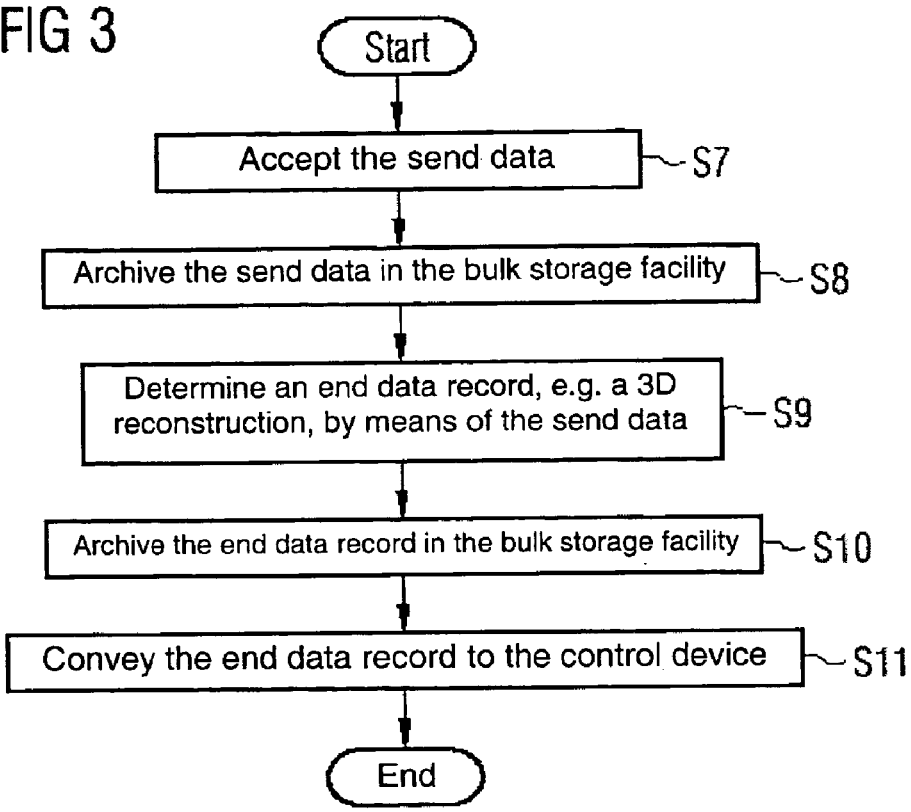
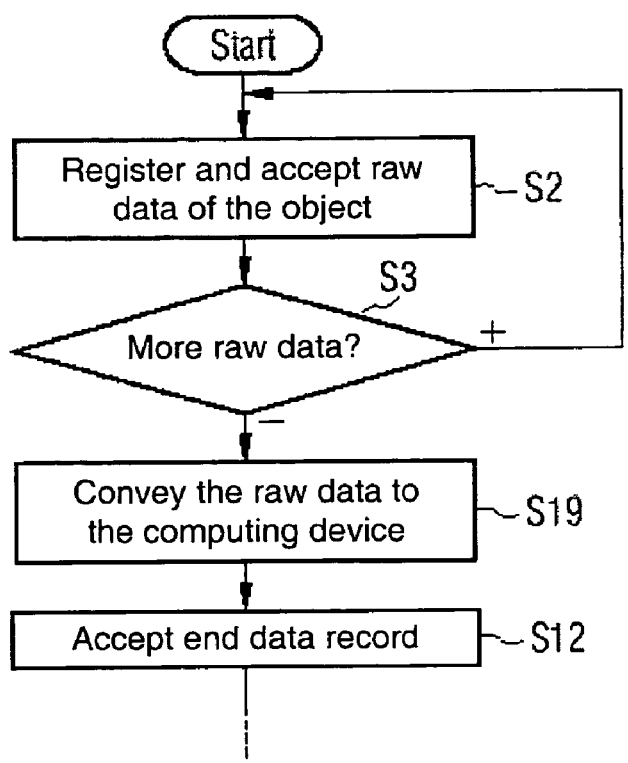

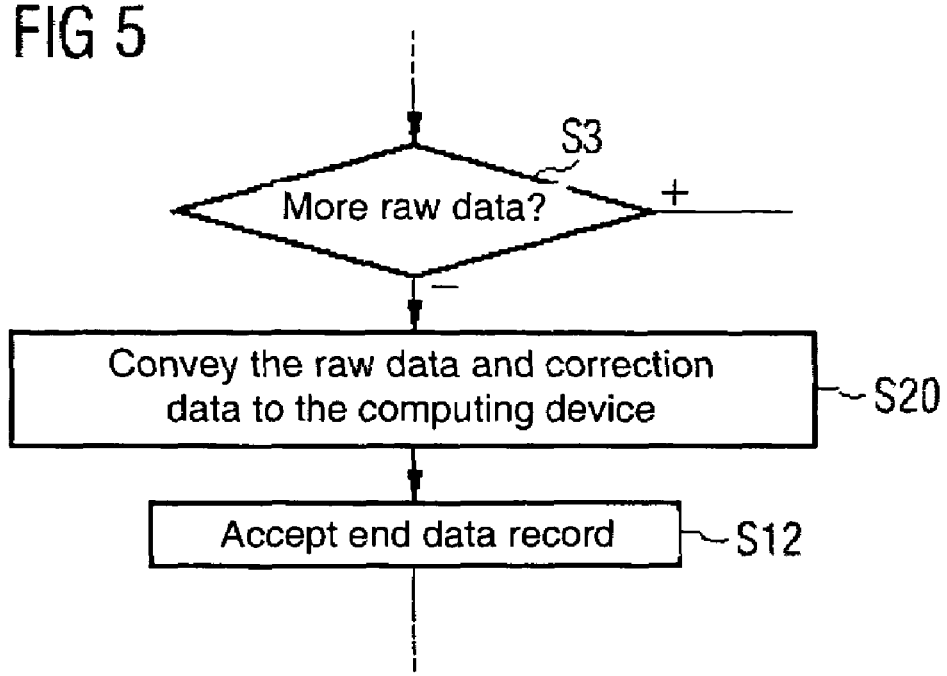
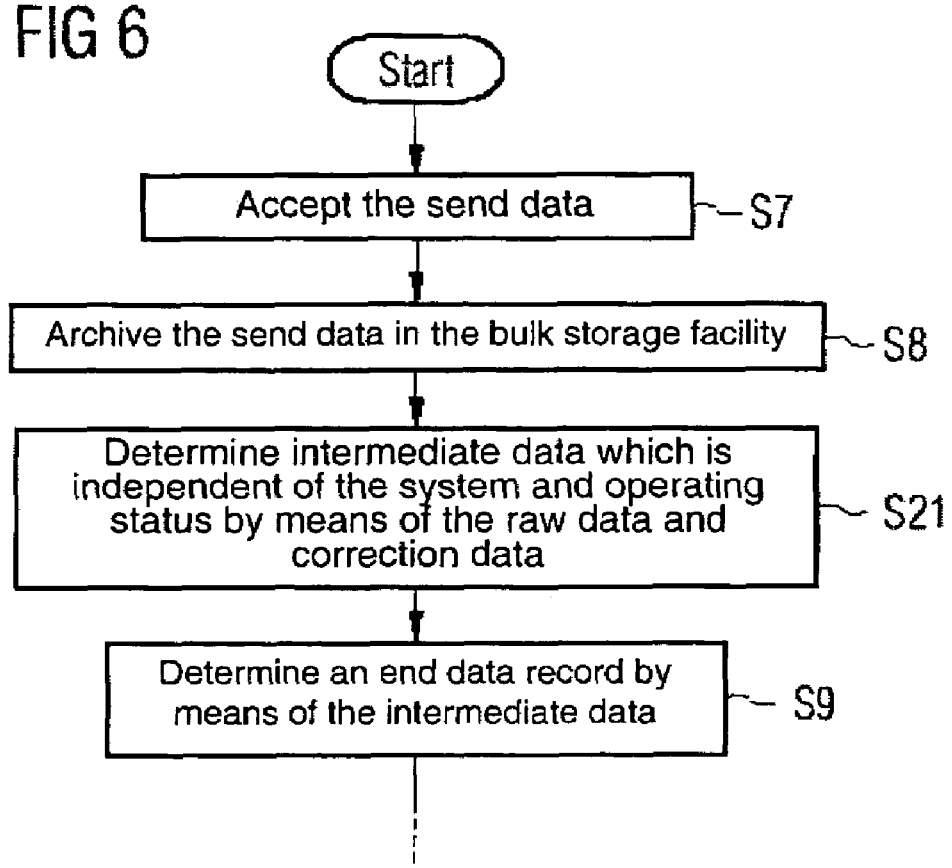

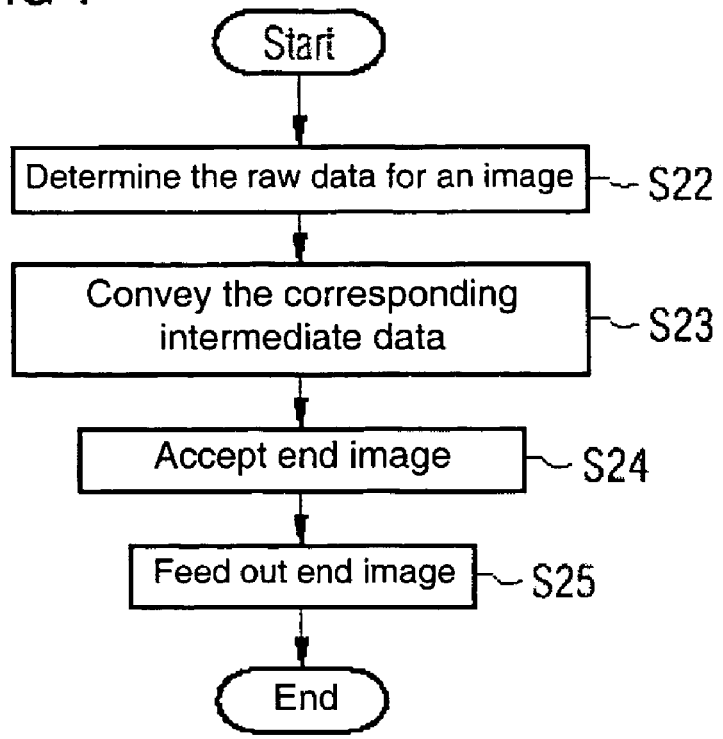
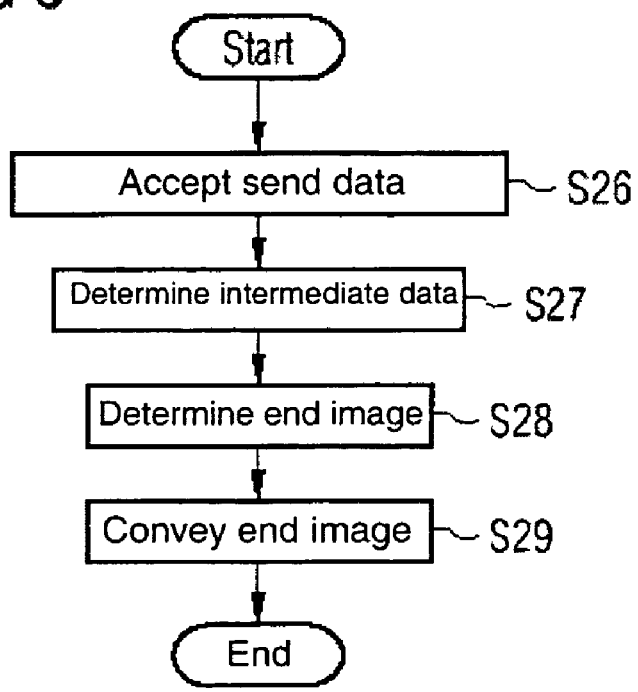

OPERATING METHODS FOR A MEDICAL IMAGING SYSTEM AND FOR A COMPUTING DEVICE, AND DEVICES CORRESPONDING THERETO

CROSS REFERENCE TO RELATED APPLICATIONS

This application claims priority to the German application No. 10342245.5, filed Sep. 11, 2003 and which is incorporated by reference herein in its entirety.

FIELD OF INVENTION

The present invention relates to an operating method for a medical imaging system, in particular an x-ray system, having at least a signal source, a detector, and a control device for the signal source and detector.

The present invention further relates to an operating method for a computing device not assigned to a medical imaging system, in particular not to an x-ray system.

The present invention furthermore relates to data media having computer programs stored thereon for implementing operating methods of this type.

The present invention also relates to a control device for a medical imaging system, in particular an x-ray system, and a computing device for implementing operating methods of this type.

The present invention finally relates to a medical imaging system, in particular an x-ray system.

BACKGROUND OF INVENTION

Medical imaging systems, in particular x-ray systems, and their control devices are generally known. The following steps are performed by the control device in said systems:
  Said control device drives the signal source and detector so that the detector registers an object's raw data,
  it accepts the registered raw data and, by means thereof, determines an end data record by which at least one end image of the object is defined, and
  via a viewing device it feeds out to a user of the medical imaging system at least one two-dimensional end image defined by the end data record.

SUMMARY OF INVENTION

Data editing is therefore located close to the system in the prior art, for which reason the control device must always be able to realize the full functionality of data editing locally.

Being highly complex, the data-editing software is expensive. It will consequently not be cost-effective to procure said software unless a commensurate amount of use is made of the system. If an incommensurate amount of use is made thereof it will take a long time to recover the procurement costs, or said costs will not be recovered at all. A further disadvantage of the prior art is that the software is also very demanding in terms of computing power. This means that the control device must also be very efficient. The procurement of this is therefore likewise very costly.

The above-cited problems become even more apparent when the medical imaging system can be operated in different modes and separate data-editing software is required for each mode.

As is generally known, software is subject to being further developed. Above and beyond the above-cited disadvantages, it is very cumbersome to distribute a new software version among all the medical imaging systems affected and to install it there.

An administration method for images produced by means of medical imaging systems is known from US-A-2002/0019751. With this method, after being produced the images are conveyed via a computer-to-computer link to a computing device not assigned to the medical imaging system and stored there centrally. They are disseminated by the computing device to other computers with no further image processing.

Therefore, it is an object of the present invention to avoid the disadvantages of the prior art cited before.

Said object is achieved by the claims.

There is thus a spatial separation of data registration and image representation on the one hand and data editing on the other. It is therefore in particular possible for the data-editing software to be used for evaluating send data originating from different medical imaging systems. Software sharing is thus possible. The advantage is that "payment" is only required for the software's actual use. "Expensive" software can, in particular, consequently also be used even if seldom required. Moreover, the control device can be embodied more cost-effectively without the user's having to tolerate a reduction in performance.

In the case of larger facilities such as hospitals, for instance, the computing device may be the property of the facility concerned. Said device is, however, frequently made available by a provider only for use in return for a charge.

The method according to the invention further also allows the data-editing software to be updated more easily because only the software located centrally in the computing device has to be updated.

In the simplest case the raw data corresponds only to a single raw data record. A raw data record can be, for instance, the raw image of a two-dimensional x-ray detector or several raw images of a one-dimensional x-ray detector which are assembled into a single two-dimensional raw image. The term "raw image" is therefore used to refer to an at least one-dimensional but generally two-dimensional raw data record.

The raw data generally contains several raw data records, however. For example it contains raw images taken from different angles.

The method according to the invention will display its advantages particularly prominently if the end data record has been determined by means of a 3D reconstruction of the object. This is because calculating the 3D reconstruction is very demanding in terms of computing power. A typical total of 40 to 400 raw data records (=two-dimensional raw images) is required for this.

In a 3D reconstruction the end image is in most cases a section through the 3D reconstruction or a parallel or perspective projection of said reconstruction. Defining the end image by means of the already existing 3D reconstruction is, however, far simpler than determining the 3D reconstruction. It is hence readily possible for the end image to be determined by the control device. It is, however, in principle also conceivable for this to be done by the computing device.

The end image has imaging parameters. Said imaging parameters are pre-specified to the control device preferably by the user interactively. This is because evaluating the 3D reconstruction will then be especially user-friendly.

As an alternative to determining a 3D reconstruction it is also possible, for example, for the end data record—despite the registration of several raw data records—to correspond to at least one end image. Several raw data records can, for example, be registered successively section-by-section in the case of a larger object and the images determined by means of the raw data records can be assembled by the computing device into a common image. In this case the number of raw images will be relatively small, being between two and eight, for instance.

It is possible for the send data to be identical to the raw data. The raw data must, however, be corrected, especially in the case of x-ray systems, to take account of correction data for the medical imaging system, said data being dependent on the system and/or operating status. It will otherwise not be possible to process the data in a meaningful manner using customary image-processing software.

There are two possibilities for enabling it to be processed using customary image-processing software:

On the one hand the send data can include the raw data and correction data. In this case the computing device will be able to determine intermediate data independent of the system and operating status by means of the raw data and correction data, and then determine the end data record by means of said intermediate data.

On the other hand the control device can also determine the intermediate data and convey said intermediate data to the computing device as send data. This is possible because the intermediate data is substantially determined by means of simple offset subtraction requiring little computing power.

The control device preferably archives at least the end data record and/or send data in a bulk storage facility. This is because this data will then also be available in the future. It is alternatively or additionally also possible for the computing device to archive the end data record and/or send data in a bulk storage facility.

BRIEF DESCRIPTION OF THE DRAWINGS

Further advantages and details will emerge from the following description of an exemplary embodiment in conjunction with the drawings. Shown in schematic form.

DETAILED DESCRIPTION OF INVENTION

Figure 1:
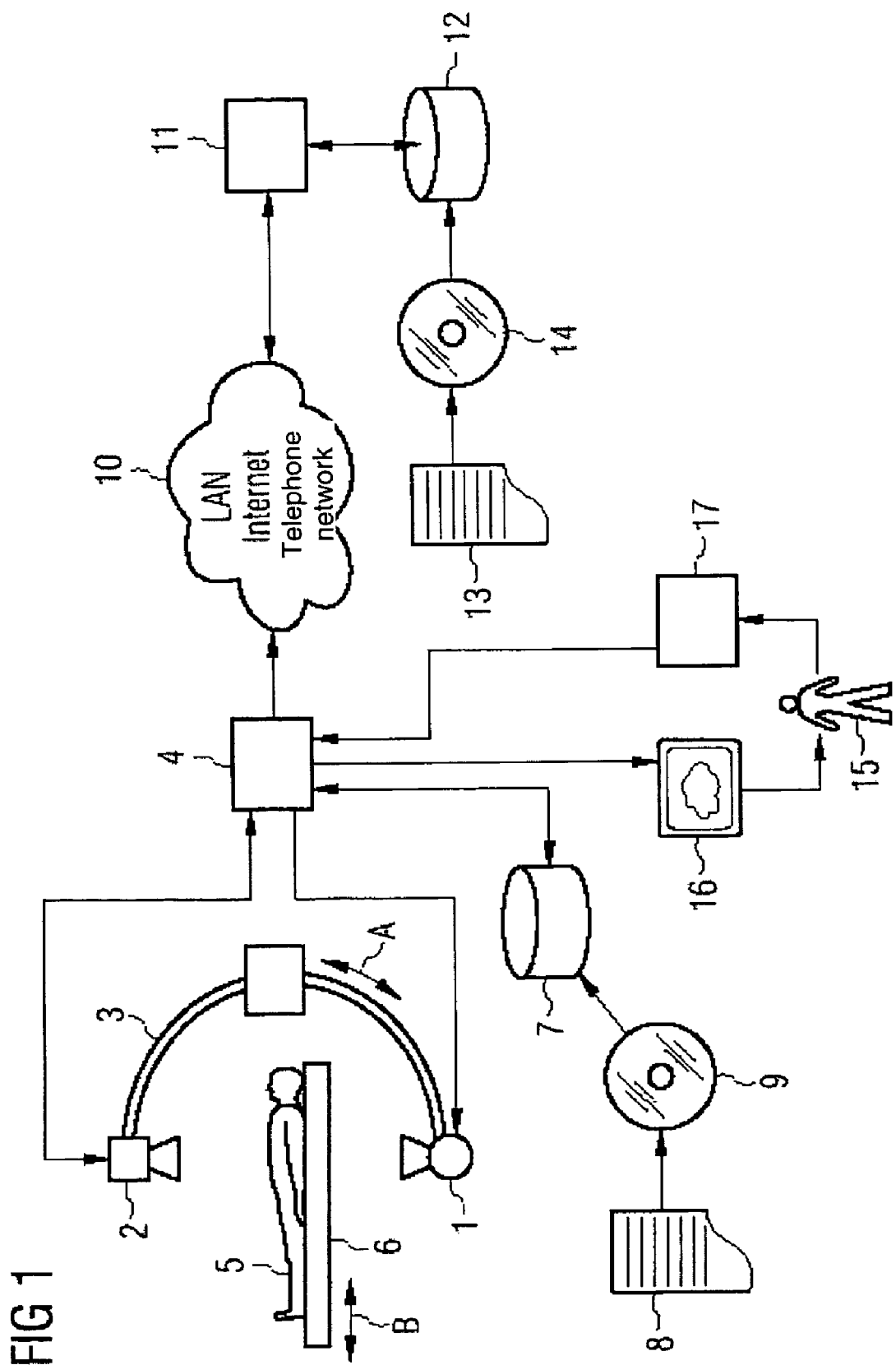
FIG. 1 a medical imaging system and its control device as well as a computing device, and FIG. 2 to 10 flowcharts.

A medical imaging system is embodied by way of example in FIG. 1 as an x-ray system. It could, however, also be embodied as another type of medical imaging system, for example a magnetic resonance imaging system, an ultrasound tomography system or a conventional ultrasound imaging system.

The x-ray system shown in FIG. 1 has an x-ray source 1 and an x-ray detector 2. The x-ray source 1 and x-ray detector 2 are located on what is termed a C arc 3.

The x-ray system further has a control device 4. Said control device 4 controls the operation of the x-ray system, in particular that of the x-ray source 1 and the x-ray detector 2. For example it swivels the x-ray source 1 and the x-ray detector 2 by moving the C arc 3 relative to an object being examined 5. This is indicated in FIG. 1 by a double arrow A.

The object being examined 5 is generally a human patient 5 positioned on an examination table 6 for the purpose of taking x-ray images. The examination table 6 can also be capable of being moved by the control device 4. This is indicated in FIG. 1 by a double arrow B.

The control device 4 has a bulk storage facility 7, for example a hard disk 7. A computer program 8 is stored in the bulk storage facility 7. The computer program 8 has previously been routed to the control device 4 via, for example, a data medium 9 (a CD-ROM 9, for instance) on which the computer program 8 is stored in (exclusively) machine-readable form. On the basis of being programmed with the computer program 8, the control device 4 operates the x-ray system in a manner which will later be explained in more detail in conjunction with FIG. 2 to 10.

The control device 4 is further connected via a computer-to-computer link 10 to a computing device 11. The computer-to-computer link 10 can be embodied in any way, for example as a local area network (LAN), an internet connection or a telephone connection. The computer-to-computer link 10 can also be embodied optionally as a wired or wireless link.

The computing device 11 is generally highly efficient in terms of performance. Examples of computing devices 11 of this type are PCs, workstations, and mainframes. The computing device 11 is not, however, permanently assigned to the x-ray system. It can in individual cases even be embodied as the control and evaluation equipment of a medical imaging system different from that shown in FIG. 1. It is, however, generally embodied as a pure computing device 11.

The computing device 11 likewise has a bulk storage facility 12, for example also a hard disk 12. Stored on the bulk storage facility 12 is a computer program 13 determining the operation of the computing device 11. The computer program 13 has likewise been previously routed to the computing device 11 via a data medium 14 (for example via a CD-ROM 14 in this case, also) on which the computer program 13 is stored in (exclusively) machine-readable form.

The control device 4 and computing device 11 interoperate as described below in conjunction with FIGS. 2 and 3 owing to programming by means of the computer programs 8, 13. FIG. 2 here relates to the operating method executed by the control device 4, and FIG. 3 relates to the operating method executed by the computing device 11.

According to a step S1 the control device 4 initially only drives the x-ray detector 2 so that the latter registers correction data; it then accepts said correction data. The correction data is here specific to the detector (hence the system) and/or operating status. It in particular represents the offset amount by which x-ray images registered later must be corrected.

In a step S2 the control device 4 then drives the x-ray source 1 and the x-ray detector 2 so that the x-ray detector 2 records raw data of the object being examined 5; it then accepts said raw data. The raw data registered in step S2 here corresponds to one two-dimensional raw image of the object 5, thus forming one raw data record.

In a step S3 the control device 4 checks whether a further raw data record is to be registered. If so, a return is made to step S2 (possibly also to step S1 as indicated in FIG. 2 by means of a dashed line). A step S4 will otherwise be carried out.

In step S4 the control device 4 determines intermediate data by means of the registered raw data and correction data. The intermediate data is here independent of the system and operating status. In a step S5 the control device 4 archives the intermediate data determined by it in the bulk storage facility 7.

The control device 4 then conveys the intermediate data to the computing device 11 in a step S6 as send data. This is of course done using the computer-to-computer link 10.

According to FIG. 3, in a step S7 the computing device 11 accepts the send data of the object 5 conveyed to it and archives said data in a step S8. In a step S9 said device then determines an end data record of the object 5 by means of the send data. The end data record can correspond to, for example, a 3D reconstruction of the object 5. Said device archives the determined end data record in a step S10, likewise in the bulk storage facility 12. Said device finally conveys the determined end data record in a step S11 back to the control device 4. This is, of course, also done using the computer-to-computer link 10.

According to FIG. 2, in a step S12 the control device 4 accepts the end data record conveyed to it and archives it in the bulk storage facility 7 in a step S13.

In a step S14 the control device 4 requests a user 15 to indicate whether a section, a perspective projection or a parallel projection of the end data record is to be shown via a viewing device 16. The viewing device 16 can be, for instance, a standard monitor or a flat display, for example what is termed a TFT display.

In a step S15 said device then requests imaging parameters of the end image from the user 15 such as, for example, a line of sight or a launch angle in the case of a perspective projection. The requested entries are fed in by the user 15 by means of a standard input device 17, for example a keyboard and/or mouse.

In accordance with the user specifications supplied in steps S14 and S15, in a step S16 the control device 4 then uses the end data record to determine the required end image. In a step S17 the end image is fed out by the control device 4 to the user 15 via the viewing device 16.

The control device 4 checks in a step S18 whether a further end image is to be fed out. If so, a return is made to step S14. The user 15 is thus able to specify the imaging parameters interactively. The method will otherwise have been concluded.

The above-described correction taking account of correction data dependent on the system and/or operating status is necessary in particular in the case of x-ray detectors 2. It is, however, also conceivable, as shown in FIG. 4, for registering of correction data not to take place. In this case the raw data will be conveyed to the computing device 11 in a step S19 (which will take the place of step S6 in FIG. 2) instead of the intermediate data. In this case the send data will therefore be identical to the raw data. However, as the computing device 11 cannot know whether the raw data or intermediate data has been conveyed to it as send data during implementation of the method described in conjunction with FIG. 3, evaluation on the part of the computing device 11 will remain unchanged. It should additionally be mentioned here that the raw data will in this case of course be archived.

An alternative possibility is, as described below in conjunction with FIG. 5, for the control device 4 to convey the correction data to the computing device 11 in a step S20 in addition to the raw data. In this case the send data will therefore comprise both the raw data and the correction data. This will enable the computing device 11 according to FIG. 6 to, in a step S21, determine the intermediate data which is independent of the system and operating status by means of the raw data and the correction data. The end data record will then of course be determined by means of the intermediate data. Step S9 in FIG. 3 can therefore be retained in unaltered form.

The end data record corresponds to the 3D reconstruction itself according to the above-described method. The end images to be shown are determined by the control device 4. It is, however, also possible for the control device 4 to request the user 15 in advance to specify the imaging parameters for one or more end representations and to convey said parameters to the computing device 11. In this case, although the computing device 11 will likewise determine the 3D reconstruction of the object 5, said 3D reconstruction of the object 5 will not yet correspond to the end data record. Rather it will be the case that the computing device 11 in this case determines a single end image or a sequence of end images by means of the 3D reconstruction of the object 5 and conveys said end image or sequence to the control device 4. In this case the control device 4 will serve solely to archive the end data record and to present it. Projection parameters cannot, however, in this case be interactively changed.

The procedure described above in conjunction with a volume reconstruction can in principle also be applied in cases where only one end image can be produced, when the end data record is hence for method-related reasons identical to the end image. For this it is possible for example according to FIG. 7 for the control device 4 to register raw data for a single image, for instance a single raw image, in a step S22. Said device will then convey corresponding send data to the computing device 11 in a step S23. Said send data can alternatively be the raw data, the raw data augmented by correction data, or intermediate data determined by means of the raw data and correction data.

The control device 4 will in this case accept the end image in a step S24 and feed it out to the user 15 in a step S25.

The computing device 11 will correspondingly accept the send data in a step S26. Said device will, where applicable, determine the intermediate data in a step S27. Said device will determine the end image in a step S28 by means of the send or intermediate data and convey said image in a step S29 back to the control device 4.

It is also possible to determine only a single end image in cases where several raw data records are required for determining the end image. This will be explained in more detail below in conjunction with FIGS. 9 and 10.

Figure 9:
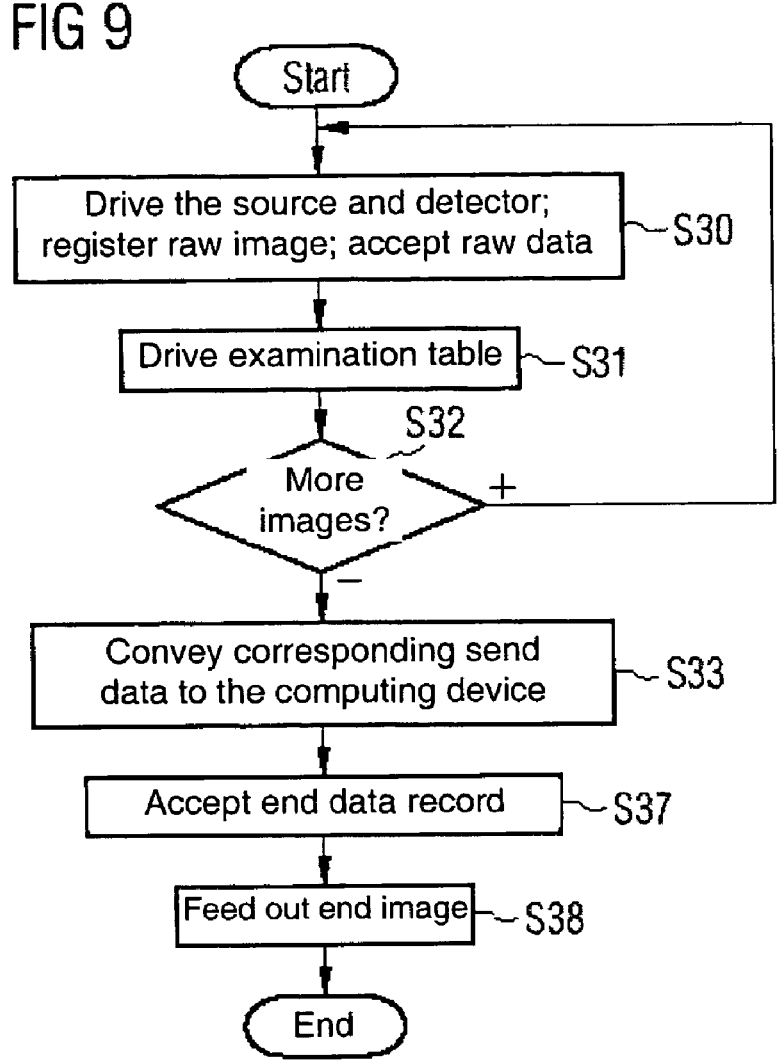

According to FIG. 9 the control device 4 drives the signal source 1 and the detector 2, for example in a step S30, so that the detector 2 registers a raw image of the object 5. The control device 4 accepts the registered raw data likewise in step S30.

In step S31 the control device 4 drives the examination table 6 so that the object being examined 5 is moved slightly. In a step S32 the control device 4 then checks whether an image sequence has now been completed or whether further images need to be taken. If further images need to be taken the control device 4 will return to step S30. It will otherwise proceed to a step S33 in which it conveys the corresponding send data of all registered raw data records to the computing device 11.

Figure 10:
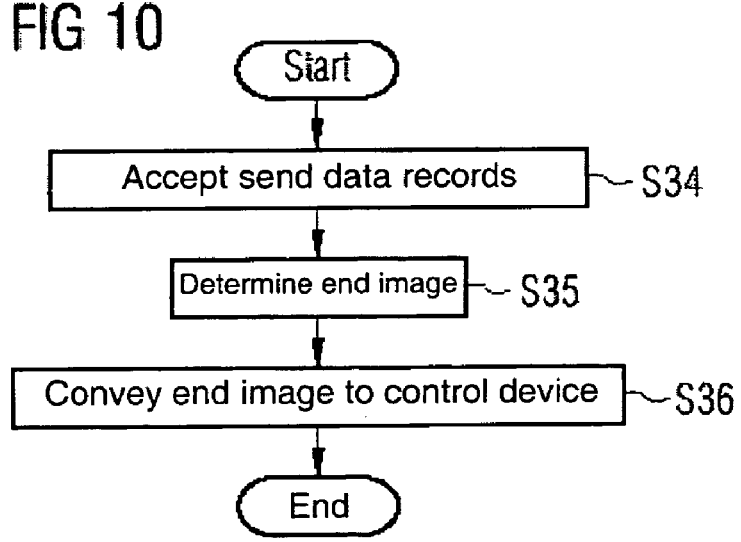

According to FIG. 10, the computing device 1 accepts the conveyed send data records in a step S34. In a step S35, said device determines an end image consisting of, for example, an assemblage of the conveyed send data records. Said device conveys said end image back to the control device 4 in a step S36.

The control device 4 accepts the end image according to FIG. 9 in a step S37 and feeds it out in a step S38 to the user 15 via the viewing device 16.

The registering of correction data and correcting of the raw data have, for clarity's sake, not been treated in detail in the above explanations of FIGS. 7 to 10. Nor has further mention been made of archiving. However, these steps are, of course, also possible in the variant embodiments according to FIGS. 7 to 10.

The invention claimed is:

1. A data medium including a computer program for performing an operating method for a medical imaging system having at least a signal source, a detector, and a control device for controlling the signal source and the detector, the method comprising:
    triggering the signal source and the detector by the control device so that the detector acquires a raw data set of an object;
    receiving the acquired raw data set by the control device;
    transmitting a transmission data set of the object, the transmission data set corresponding to the acquired raw data set, via a computer-to-computer link to a computing device, the computing device not being assigned to the medical imaging system, by the control device;
    receiving an end data set from the computing device by the control device via the computer-to-computer link, the end data set being processed by the computing device using the transmission data set;
    requesting a first input from a user of the medical imaging system if a section, a perspective projection, or a parallel projection of the end data set is to be displayed by the control device;
    requesting a second input from the user of the medical imaging system, the second input being an imaging parameter of a two-dimensional end image by the control device;
    determining the two-dimensional end image based upon the end data set and the first and second inputs by the control device; and
    displaying the two-dimensional end image to the user of the medical imaging system via a display device, by the control device, wherein
    the computer program includes software code adapted to perform the method.

2. A control device for a medical imaging system, having at least a signal source, a detector, a control device for controlling the signal source and the detector, and a bulk memory device including a computer program for operating the medical imaging system by the control device, the operation comprising:
    triggering the signal source and the detector by the control device so that the detector acquires a raw data set of an object;
    receiving the acquired raw data set by the control device;
    requesting an imaging parameter of a two-dimensional end image by the control device from the user of the medical imaging system;
    transmitting a transmission data set of the object, the transmission data set corresponding to the acquired raw data set, and the imaging parameter of the two-dimensional end image, via a computer-to-computer link to a computing device, the computing device not being assigned to the medical imaging system, by the control device;
    receiving the two-dimensional end image from the computing device by the control device via the computer-to-computer link, the two-dimensional end image being determined by the computing device based on the transmitted imaging parameter and an end data set, the end data set being processed by the computing device using the transmission data set; and
    displaying the two-dimensional end image to the user of the medical imaging system via a display device, by the control device.

3. A medical imaging system having at least a signal source and a detector, comprising:
    a bulk memory device including a computer program for operating the medical imaging system;
    a control device for controlling the signal source and the detector, and for operating the medical imaging system using the computer program, the operation comprising:
    triggering the signal source and the detector by the control device so that the detector acquires a raw data set of an object;
    receiving the acquired raw data set by the control device;
    transmitting a transmission data set of the object, the transmission data set corresponding to the acquired raw data set, via a computer-to-computer link to a computing device, the computing device not being assigned to the medical imaging system, by the control device;
    receiving an end data set from the computing device by the control device via the computer-to-computer link, the end data set being processed by the computing device using the transmission data set;
    requesting an imaging parameter of a two-dimensional end image by the control device from the user of the medical imaging system;
    determining the two-dimensional end image based upon the end data set and the imaging parameter by the control device; and
    displaying the two-dimensional end image to the user of the medical imaging system via a display device, by the control device.

4. The medical imaging system according to claim 3, wherein the end data set includes a 3D reconstruction of the object and the end image is a section, a perspective projection, or a parallel projection of the 3D reconstruction.

5. An operating method for a computing device, comprising the following steps:
    receiving a transmission data set of an object from a control device via a computer-to-computer link, the control device being adapted to control a medical imaging system, by the computing device;
    calculating an end data set using the received transmission data set, by the computing device, the end data set including at least one two-dimensional end image of the object;
    archiving the transmission data set and the end data set in a bulk memory device connected to the computing device; and
    transmitting the end data set to the control device via the computer-to-computer link, by the computing device, wherein
    the computing device is not assigned to the medical imaging system.

6. The operating method according to claim 5, wherein the transmission data set includes a single transmission data set.

7. The operating method according to claim 6, wherein the end data set corresponds to at least one end image.

8. The operating method according to claim 5, wherein the transmission data set includes a plurality of transmission data sets.

9. The operating method according to claim 8, wherein the end data set corresponds to a 3D reconstruction of the object.

10. The operating method according to claim 8, wherein the end data set corresponds to at least one end image.

11. The operating method according to claim 5, wherein the transmission data set includes a raw data set of the object and a correction data set relating to any of the medical imaging system and the operating status of the medical imaging system, wherein the computing device calculates an intermediate data set using the raw data set and the correction data set, the intermediate data set being independent of the medical imaging system and its operating status, and wherein the computing device calculates the end data set using the intermediate data set.

12. The operating method according to claim 11, wherein the transmission data set further comprises an imaging parameter of a two-dimensional end image which is input by the user of the medical imaging system.

13. The operating method according to claim 12, wherein the computing device further determines the two-dimensional end image based upon the end data set and the imaging parameter.

14. A data medium having a computer program for performing an operating method for a computing device, the operating method comprising:

receiving a transmission data set of an object from a control device via a computer-to-computer link, the control device being adapted to control a medical imaging system, by the computing device;

calculating an end data set using the received transmission data set by the computing device;

determining a two-dimensional end image of the object by the computing device based on the end data set and an imaging parameter of the end image, the imaging parameter being specified by a user of the medical imaging system and transmitted to the computing device via the computer-to-computer link;

transmitting the end image to the control device via the computer-to-computer link, by the computing device, wherein the computing device is not assigned to the medical imaging system, and wherein the computer program includes software code adapted to perform the method.

15. A computing device having a bulk memory device including a computer program for operating the computer device, the computing device configured to perform, upon executing said computer program, the steps of:

receiving a transmission data set of an object from a control device via a computer-to-computer link, the control device being adapted to control a medical imaging system, by the computing device;

calculating an end data set using the received transmission data set, by the computing device, the end data set including at least one two-dimensional end image of the object;

archiving the end data set in the bulk storage device; and transmitting the end data set to the control device via the computer-to-computer link, by the computing device, wherein the computing device is not assigned to the medical imaging system.

\* \* \* \* \*